United States Patent [19]

Hunter

[11] 4,074,111
[45] Feb. 14, 1978

[54] VAPORIZING ATTACHMENT FOR LIGHT BULBS

[76] Inventor: William George Hunter, 704 Kingsmere Cresc. SW., Calgary, Canada

[21] Appl. No.: 762,864

[22] Filed: Jan. 27, 1977

[51] Int. Cl.² .............................. F22B 1/28; A61L 3/00
[52] U.S. Cl. .......................................... 219/275; 21/120
[58] Field of Search .................. 219/275, 276; 21/114, 21/117, 119, 120

[56] References Cited

U.S. PATENT DOCUMENTS

| 1,403,548 | 1/1922 | Gudeman | 219/275 X |
| 2,468,164 | 4/1949 | Brewster | 21/120 |
| 2,539,696 | 1/1951 | Morrison | 21/120 |

FOREIGN PATENT DOCUMENTS

| 463,305 | 12/1913 | France | 21/119 |
| 415,890 | 9/1934 | United Kingdom | 21/119 |

*Primary Examiner*—C. L. Albritton
*Attorney, Agent, or Firm*—Stanley G. Ade

[57] ABSTRACT

A shroud is detachably engaged around the neck of a light bulb and is detachably sealed to the bulb at this point so that it is leakproof. The shroud extends upwardly around the bulb and is spaced therefrom. Liquid or crystal fragrance, deodorant, insecticide or the like is poured into the lower portion of the shroud surrounding the light bulb so that when lit, the heat from the bulb vaporizes the liquid or crystals and the vapor is dispersed from the open upper end of the shroud by convection air currents. An elastomeric O-ring is in wedging contact between the lower end of the light bulb and the lower end of the shroud immediately above the sealing material in order to protect the sealing material from liquids within the shroud.

2 Claims, 4 Drawing Figures

VAPORIZING ATTACHMENT FOR LIGHT BULBS

BACKGROUND OF THE INVENTION

This invention relates to new and useful improvements in fragrance devices in which perfume, essence or crystals may be placed within a reservoir in contact with the heat generated by an electric bulb when illuminated so that convection currents carry the fragrance upwardly into the surrounding atmosphere.

Although the term "fragrance" is used throughout the specification, nevertheless it should be appreciated that the liquid or crystals being evaporated can be a fragrance, insecticide, medicament or the like.

It is an object of the invention to provide a device of the character herewithin described in which various fragrances or the like can be permeated through the area within which the light bulb is being used in order to mask the odors of cooking, smoke or the like, or to provide medicated vapors or insecticidal vapors as desired.

Another object of the invention is to provide a device of the character herewithin described in which a variety of fragrances can be used either perfume fragrances or such fragrances as pine, balsam or the like.

Another object of the invention is to provide a device of the character herewithin described which includes means to seal the adhesive from contact with the liquids within the reservoir so that deterioration cannot take place which might cause noxious vapors to be disseminated.

Another object of the invention is to provide a device of the character herewithin described which is simple in construction, economical in manufacture and otherwise well suited to the purpose for which it is designed.

With the foregoing objects in view, and other such objects and advantages as will become apparent to those skilled in the art to which this invention relates as this specification proceeds, my invention consists essentially in the arrangement and construction of parts all as hereinafter more particularly described, reference being had to the accompanying drawings in which:

DESCRIPTION OF THE DRAWINGS

In the drawings like characters of reference indicate corresponding parts in the different figures.

DETAILED DESCRIPTION

Figure 1:
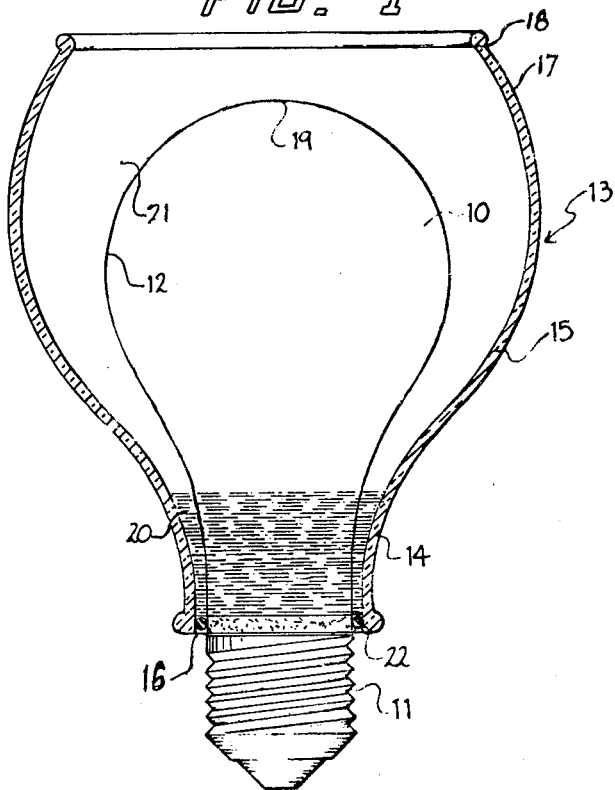
FIG. 1 is a side elevation of the device with the shroud sectioned for clarity.
Figure 4:
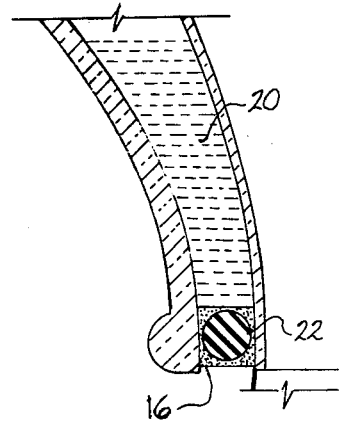
FIG. 4 is an enlarged fragmentary cross sectional view showing the O-ring and the epoxy resin seal.
Figure 2:
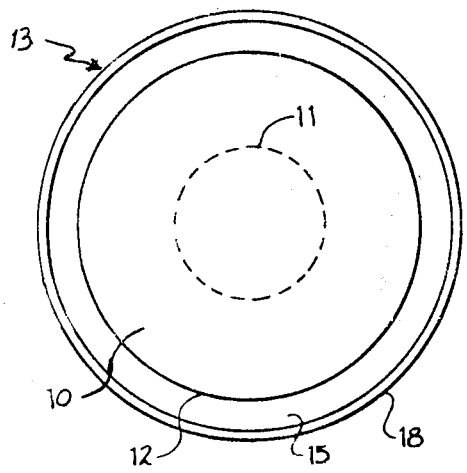
FIG. 2 is a top plan view of FIG. 1.
Figure 3:
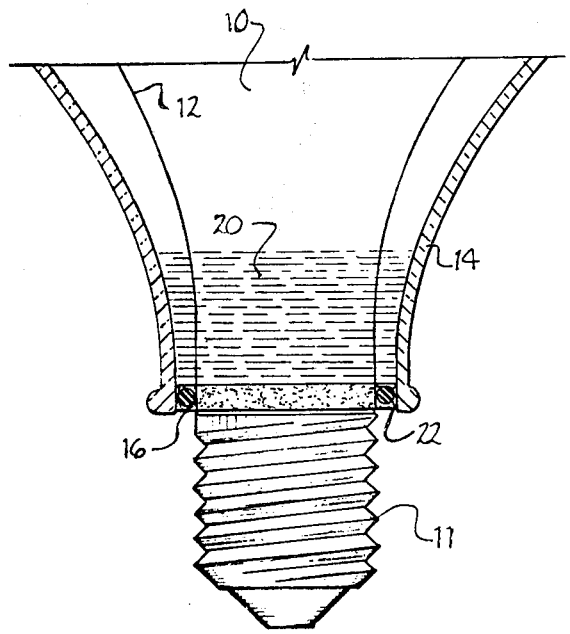
FIG. 3 is an enlarged fragmentary partially sectioned view of the lower end of FIG. 1.

Proceeding therefore to describe the invention in detail, reference character 10 shows a conventional light bulb which includes the metal screw threaded base 11 and the evacuated envelope 12 carrying the conventional filament (not illustrated) which supplies light, together with heat.

A shroud collectively designated 13 is formed preferably from clear or opaque heat resistant glass and is circular in configuration when viewed in plan. This envelope or shroud includes a minor or lower end portion 14 and a major or upper end portion 15. The open minor or lower end portion 14 is adapted to engage around the base of the glass envelope 12 just above the junction of the base to the meal screw threaded portion 11 and spaced slightly therefrom and is secured as will hereinafter be described.

The diameter of the shroud increases as it passes from the minor end towards the major end portion 15 and then decreases slightly at the upper open end 17 terminating in a rolled bead 18 as clearly shown.

It should be observed that this upper open end terminates above the upper end 19 of the electric bulb to which it is secured, as clearly shown in FIG. 1.

The lower or minor end 14 of the shroud, being spaced from the relevant portion of the glass envelope 12, defines a fragrance reservoir 20 and the major end portion 15 together with the relevant portion of the glass envelope 12 defines a fragrance evaporating chamber 21 and the englobement characteristics of this major portion and upper end of the shroud permits this chamber, to a certain extent, to restrain the escape of the fragrance so that it is controlled within limits.

It is desirable that the lower or minor end portion 14 of the shroud be manufactured of a frosted glass (not illustrated) although the major end portion 15 may be clear glass or opaque as desired. An advantage of the frosted glass is that the upper limits of this frosting may be used as a guideline for the liquid essence used for evaporating purposes.

A conventional epoxy resin can be used to secure the shroud 13 to the envelope 12 at the lower end thereof and a further seal is provided which, in this embodiment, takes the form of an elastomeric O-ring 22 surrounding the glass envelope of the electric light bulb and being in wedging contact with the inner surface of the lower portion or ring of the reservoir 20. The epoxy resin 16 adhesively secures the O ring to the light bulb envelope 12 and to the shroud 13 and is usually baked on at a temperature of approximately 1200° F depending upon the type of epoxy resin used.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What I claim as my invention is:

1. An article of manufacture comprising in combination a vaporizing shroud and an electric light bulb, said electric light bulb including an envelope and a metal screw threaded base secured to one end of the envelope, said shroud including an open lower, relatively small, reservoir end portion and an open upper, relatively large, evaporating portion, means to detachably secure said shroud by the lower end thereof around the portion of said envelope adjacent said metal base whereby said shroud is sealably secured to said envelope and extends upwardly therefrom in spaced relationship, said lower end portion forming an annular reservoir around said light bulb, said upper end portion forming an evaporating chamber above said reservoir and means to sealably secure said shroud to said light bulb, said last mentioned means including epoxy resin adhesive between said lower small end of said shroud and the associated portion of said envelope above said metal base and a flexible elastomeric O ring surrounding said associated portion of said envelope and within said epoxy resin and being in wedging contact with the inner surface of said lower small end of said shroud thereby sealing said lower small end to said envelope.

2. The article according to claim 1 in which said shroud increases in diameter from said lower end thereof through the upper end portion thereof and then decreases in diameter slightly at said upper end, said upper end terminating above the other end of said light bulb envelope.

* * * * *